(12) United States Patent
Lee et al.

(10) Patent No.: US 9,907,522 B2
(45) Date of Patent: Mar. 6, 2018

(54) RADIATION DIAGNOSTIC APPARATUS

(71) Applicant: SAMSUNG ELECTRONICS CO., LTD., Suwon-si, Gyeonggi-do (KR)

(72) Inventors: Jeong-pil Lee, Suwon (KR); Su-young Ko, Hwaseong (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 527 days.

(21) Appl. No.: 14/294,739

(22) Filed: Jun. 3, 2014

(65) Prior Publication Data

US 2015/0126863 A1    May 7, 2015

(30) Foreign Application Priority Data

Nov. 6, 2013  (KR) .................. 10-2013-0134365

(51) Int. Cl.
 *A61B 6/00* (2006.01)
 *A61B 6/04* (2006.01)

(52) U.S. Cl.
 CPC .......... *A61B 6/4429* (2013.01); *A61B 6/4441* (2013.01); *A61B 6/4482* (2013.01); *A61B 6/0407* (2013.01); *A61B 6/0457* (2013.01)

(58) Field of Classification Search
 USPC ....................................................... 600/436
 See application file for complete search history.

(56) References Cited

U.S. PATENT DOCUMENTS

| 4,979,202 | A | 12/1990 | Siczek et al. | |
| 5,572,568 | A * | 11/1996 | Kanemitsu | A61B 6/08 378/190 |
| 5,615,450 | A * | 4/1997 | Butler | B60B 33/00 16/18 CG |
| 6,205,347 | B1 * | 3/2001 | Morgan | A61B 6/04 600/407 |
| 6,315,446 | B1 | 11/2001 | Kidd et al. | |
| 6,789,941 | B1 * | 9/2004 | Grady | A61B 6/4233 378/196 |
| 7,300,204 | B2 | 11/2007 | Gotoh | |
| 7,534,036 | B2 | 5/2009 | Delmas et al. | |
| 7,744,277 | B2 | 6/2010 | Noda et al. | |
| 7,991,118 | B2 | 8/2011 | Noordhoek | |
| 2002/0080921 | A1 * | 6/2002 | Smith | A61B 6/0457 378/189 |
| 2008/0189859 | A1 * | 8/2008 | Sloan | A61N 5/10 5/601 |

(Continued)

FOREIGN PATENT DOCUMENTS

EP   0 224 886 A1   6/1987

*Primary Examiner* — Joel F Brutus
(74) *Attorney, Agent, or Firm* — Staas & Halsey LLP

(57) ABSTRACT

Disclosed is a radiation diagnostic apparatus that includes an examination table that has a length in a first direction, a fixing frame that is fixedly disposed on a floor to be separated from the examination table in the first direction and includes a guide member provided in the first direction, a transfer frame that contacts the guide member and moves along the first direction with respect to the fixing frame, a first rotary arm that is rotatably connected to the transfer frame, and a second rotary arm that is rotatably connected to the first rotary arm and is provided for a radiation source and a radiation detector to face each other.

16 Claims, 11 Drawing Sheets

(56) References Cited

U.S. PATENT DOCUMENTS

2011/0222667 A1* 9/2011 Gregerson ............. A61B 6/035
378/198
2012/0104283 A1* 5/2012 Dirauf .................. A61N 5/1082
250/492.1

* cited by examiner

RADIATION DIAGNOSTIC APPARATUS

RELATED APPLICATIONS

This application claims the benefit of Korean Patent Application No. 10-2013-0134365, filed on Nov. 6, 2013, in the Korean Intellectual Property Office, the disclosure of which is incorporated herein in its entirety by reference.

BACKGROUND

1. Field

One or more embodiments relate to a movable floor type radiation diagnostic apparatus.

2. Description of the Related Art

Examples of an imaging system of a medical diagnostic apparatus may include various imaging modalities such as an X-ray system, a computerized tomography (CT) system, an ultrasound system, an electronic beam tomography system, a magnetic resonance system.

The imaging system includes a radiation source and a radiation detector that are disposed to face each other. Radiation irradiated from the radiation source passes through a patient and reaches the radiation detector. The radiation detector detects variable attenuation of received radiation to generate an image.

For angiography, it is required to generate an image over a certain region in a height direction of a patient. To this end, in the related art, an examination table with a patient located thereon moves in a length direction of the examination table or a height direction of a patient. However, since the examination table moves, anxiety is caused to or in a patient, causing a reduction in accuracy of a diagnosis.

SUMMARY

One or more embodiments include a radiation diagnostic apparatus that solves anxiety of a patient, and enables an accurate diagnosis.

One or more embodiments include a floor type radiation diagnostic apparatus in which an imaging system moves in a length direction of an examination table, and a moving path of a worker around the table is sufficiently secured and safely available when the radiation diagnostic apparatus is not used.

Additional aspects will be set forth in part in the description which follows and, in part, will be apparent from the description, or may be learned by practice of the presented embodiments.

According to one or more embodiments, a radiation diagnostic apparatus includes: an examination table that has a length in a first direction; a fixing frame that is fixedly disposed on a floor to be separated from the examination table in the first direction, and includes a guide member formed along the first direction; a transfer frame that contacts the guide member, and moves along the first direction with respect to the fixing frame; a first rotary arm that is rotatably connected to the transfer frame; and a second rotary arm that is rotatably connected to the first rotary arm, and is provided for a radiation source and a radiation detector to face each other.

The transfer frame may move to a first position, at which a front end of the transfer frame overlaps the fixing frame, and a second position at which the front end of the transfer frame deviates from or does not overlap the fixing frame.

When the transfer frame is disposed at the first position, respective front ends of the transfer frame and the first and second rotary arms may be disposed farther away from the examination table than a front end of the fixing frame.

When the transfer frame is disposed at the second position, a front end of the transfer frame may be disposed closer to the examination table than a front end of the fixing frame.

The radiation diagnostic apparatus may further include at least one rolling member that supports a weight of the transfer frame, and rotates according to movement of the transfer frame.

The radiation diagnostic apparatus may further include a supporting member that supports the rolling member, is formed to be extended in the first direction, and is disposed on the floor for a top of the supporting member to match a surface of the floor.

The radiation diagnostic apparatus may further include a sweeping member that removes foreign materials from the supporting member.

The fixing frame may be disposed to be separated from the examination table in a second direction intersecting the first direction.

According to one or more embodiments, a radiation diagnostic apparatus includes: an examination table that has a length in a first direction; a fixing frame that is buried in and fixed to a floor not to protrude from a surface of the floor, and includes at least one guide groove formed in the first direction; a transfer frame that includes a moving member inserted into the guide groove, and moves along the first direction with respect to the fixing frame; a first rotary arm that is rotatably connected to the transfer frame; and a second rotary arm that is rotatably connected to the first rotary arm, and is provided for a radiation source and a radiation detector to face each other.

The moving member may include a rolling member that is rotatable and a supporting shaft that supports the rolling member, and the guide groove may include a first region in which the rolling member moves and a second region in which the supporting shaft moves.

In the guide groove, a width of the second region may be narrower than a width of the first region.

The radiation diagnostic apparatus may further include a blocking member that is provided in the second region, and prevents foreign materials from penetrating from an outside.

The transfer frame may further include a sweeping member that removes internal foreign materials of the guide groove.

The fixing frame may be disposed to be separated from the examination table in a second direction intersecting the first direction.

The guide groove may include a first guide groove and a second guide groove that is separated from the first guide groove in a second direction intersecting the first direction.

The fixing frame may include: a first fixing frame in which the first guide groove is formed; and a second fixing frame in which the second guide groove is formed.

The fixing frame may be a single member in which the first and second guide grooves are formed.

The fixing frame may extend in the first direction for at least one portion of the fixing frame to overlap the examination table, and the examination table may be disposed on a top of the fixing frame.

The transfer frame may include a shaking prevention member that prevents the transfer frame from being shaken in a direction intersecting the first direction.

The shaking prevention member may include a side shaking prevention member that contacts both sides of the guide groove, and rotates according to movement of the transfer frame.

The shaking prevention member may include an upper shaking prevention member that contacts a top of the guide groove, and rotates according to movement of the transfer frame.

According to one or more embodiments an apparatus may include a patient examination table fixed to a position of a floor and a diagnostic apparatus movable along the floor to confront a patient on the table, where the table need not move as the diagnostic apparatus is moved relative to the patient and the diagnostic apparatus retracts away from the table to allow a free path for a worker around the table.

The diagnostic apparatus may include a cart that moves along the floor and an imaging system carried by the cart to image the patient.

The cart may have wheels that roll on a surface level with the floor where the diagnostic apparatus may further include a stabilization frame fixed to the floor and having a guide that mates with the cart to stabilize the cart when moving.

The cart may also have wheels that roll on a surface buried within the floor and may further include a guide embedded in the floor in which the wheels roll.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
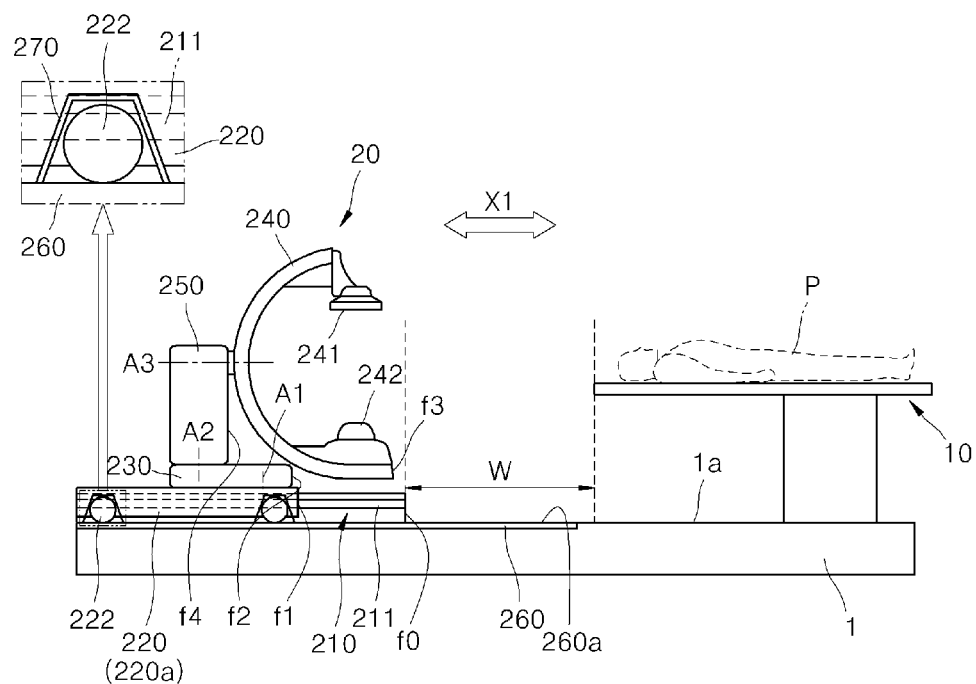
FIG. 1 is a view conceptually illustrating a radiation diagnostic apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, a configuration and an operation of a radiation diagnostic apparatus according to embodiments thereof will be described in detail with reference to the accompanying drawings. In the following embodiments, it will be understood that although the terms first, second, and third are used herein to describe various elements, these elements should not be limited by these terms. These terms are only used to distinguish one element from another element.

Figure 2:
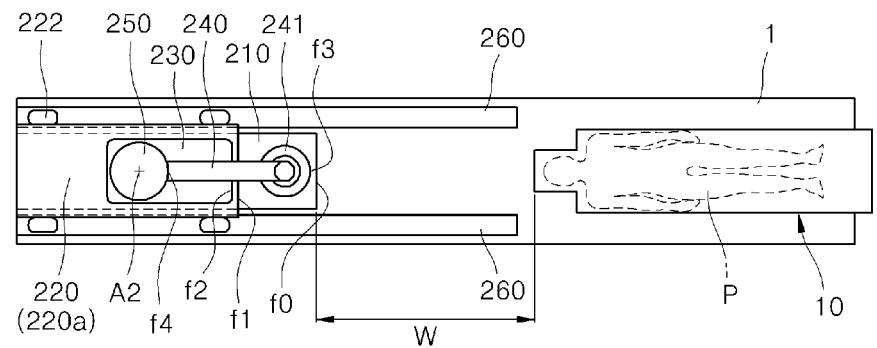
FIG. 2 is a plan view illustrating the radiation diagnostic apparatus of FIG. 1.

FIG. 1 is a view conceptually illustrating a radiation diagnostic apparatus according to an embodiment, and FIG. 2 is a plan view illustrating the radiation diagnostic apparatus of FIG. 1. Referring to FIGS. 1 and 2, the radiation diagnostic apparatus includes an examination table 10 and an imaging system 20 that generates an image of an object P located on the examination table 10.

The examination table 10 has a length that enables the object P to be located thereon. A length direction X1 (hereinafter referred to as a first direction) of the examination table 10 is parallel to a length or height direction of the object P. The object P may be, for example, a patient or a part of the patient. The examination table 10 is an element separate from the imaging system 20, and may be supported by a floor 1. The examination table 10 may be fixed to the floor 1, or may be movably supported. For example, the examination table 10 may be vertically moved to raise or lower the object P, and may be horizontally moved in the length direction X1 of the object P but need not do so during an examination.

The imaging system 20 includes a radiation source 241 and a radiation detector 242 that are disposed to face each other. The examination table 10 may be disposed between the radiation source 241 and the radiation detector 242. The radiation source 241 irradiates radiation onto the object P located on the examination table 10, and the radiation detector 242 analyzes the radiation passing through the object P to process an image of the object P. The radiation source 241 may be, for example, an X-ray source that emits X-ray. The radiation detector 242 may be, for example, an X-ray detector that detects the X-ray. However, the type of each of the radiation source 241 and the radiation detector 242 may be appropriately changed depending on the case.

The imaging system 20 includes a fixing frame 210 that is fixedly disposed on the floor 1, a transfer frame 220 (or a type of cart) that is movably disposed at or on the fixing frame 210, a first rotary arm 230, a second rotary arm 240, and a third rotary arm 250. The imaging system 20 includes a driving member (not shown), which drives the transfer frame 220, and a driving member (not shown) that rotates the first to third rotary arms 230, 240 and 250.

The second rotary arm 240 may be a C-arm that includes the radiation source 241 and the radiation detector 242. The second rotary arm 240 may be pivot-connected to the third rotary arm 250 to be rotatable with respect to a third axis A3.

The first rotary arm 230 is connected to the second rotary arm 240. The first rotary arm 230 may support the third rotary arm 250 in order for the third rotary arm 250 to rotate with respect to a second axis A2. The second axis A2 may intersect the third axis A3. The third rotary arm 250 may be pivot-connected to the first rotary arm 230. The third rotary arm 250 may support the second rotary arm 240 to be rotatable with respect to the third axis A3, and may rotate with respect to the second axis A2 about the first rotary arm 230. The third rotary arm 250 is an optional element, and may not be provided, in which case the second rotary arm 240 may be directly connected to the first rotary arm 230.

The transfer frame 220 may support the first rotary arm 230 in order for the first rotary arm 230 to rotate with respect to a first axis A1. The first rotary arm 230 may be pivot-connected to the transfer frame 220. The first axis A1 may be parallel to the second axis A2.

Figure 3:
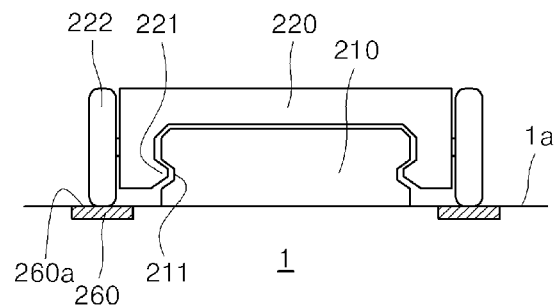
FIG. 3 is a front view schematically illustrating a connection relationship between a transfer frame and a fixing frame which are illustrated in FIG. 1.

The transfer frame 220 may be connected or coupled to the fixing frame 210, which may help to stabilize the transfer frame 220, and may be movable along the first direction X1. FIG. 3 is a front view schematically illustrating a connection or coupling relationship between the transfer frame 220 and the fixing frame 210 which are illustrated in FIG. 1. Referring to FIGS. 1 and 3, a guide rail structure may be provided between the transfer frame 220 and the fixing frame 210. As an example of the guide rail structure, a guide member 211 that guides movement of the transfer frame 220 in the first direction X1 may be provided at both sides of the fixing frame 210 in the first direction X1. The guide member 211 may extend along the first direction X1. A moving member 221 (see FIG. 3) that moves along the guide member 211 in contact with the guide member 211 may be provided at or on the transfer frame 220. The moving member 211 may have a shape corresponding to the guide member 211. For example, when the guide member 211 has a concave shape, the moving member 221 may have a convex shape that may be inserted into the guide member 211. However, the shapes of the moving member 221 and the guide member 211 are not limited thereto, and the moving member 221 and the guide member 211 may have various shapes corresponding to and that mate with each other. Also, although not shown, a ball bearing may be provided between the moving member 221 and the fixing frame 210 so as to enable the moving member 221 to be smoothly and relatively moved.

When the moving member 221 of the transfer frame 220 moves along the guide member 211, the transfer frame 220 moves along the first direction X1.

The transfer frame 220 may include at least one rolling member 222 (for example, a wheel) that supports a weight of the transfer frame 220, and rotates according to movement of the transfer frame 220. For example, a plurality of the rolling members 222 may be respectively disposed at both sides of the transfer frame 220.

As described above, the imaging system 20 includes the transfer frame 220 that moves in the first direction X1 with respect to the fixing frame 210, and thus, even without moving the examination table 10 on which the object P is located, the imaging system 20 may generate an image of the object P along the length direction X1 of the object P. Since an image of the object P in the length direction X1 is generated without moving the examination table 10, anxiety of the object P is solved, and a more accurate diagnosis of the object P is achieved.

The present embodiments relate to a floor type radiation diagnostic apparatus in which the imaging system 20 that moves in the first direction X1 is disposed on the floor 1. Since the radiation diagnostic apparatus has a structure in which the imaging system 20 is disposed on the floor 1, it is required to consider a moving route of a patient or a worker (for example, a doctor or a nurse). Also, it is required to consider a moving path through which the other medical apparatus moves.

The fixing frame 210 is disposed to be separated from the examination table 10 in the first direction X1. Therefore, a certain distance W is secured or provided between the fixing frame 210 and the examination table 10, and thus, a moving route or path of a worker or a patient around the table 10 is ensured or provided. A separation distance W between the fixing frame 210 and the examination table 10 may be about 1 m or less in consideration of that the second rotary arm 240 is needed to overlap the examination table 10.

The transfer frame 220 may move in a front direction (which becomes closer to the examination table 10) or a rear direction (which deviates or moves away from the examination table 10) along the first direction X1 with respect to the fixing frame 210. For example, the transfer frame 220 may move to a first position 220a, at which a front end f1 of the transfer frame 220 overlaps the fixing frame 210, and a second position 220b at which the front end f1 of the transfer frame 220 deviates or is separate from the fixing frame 210.

Figure 4:
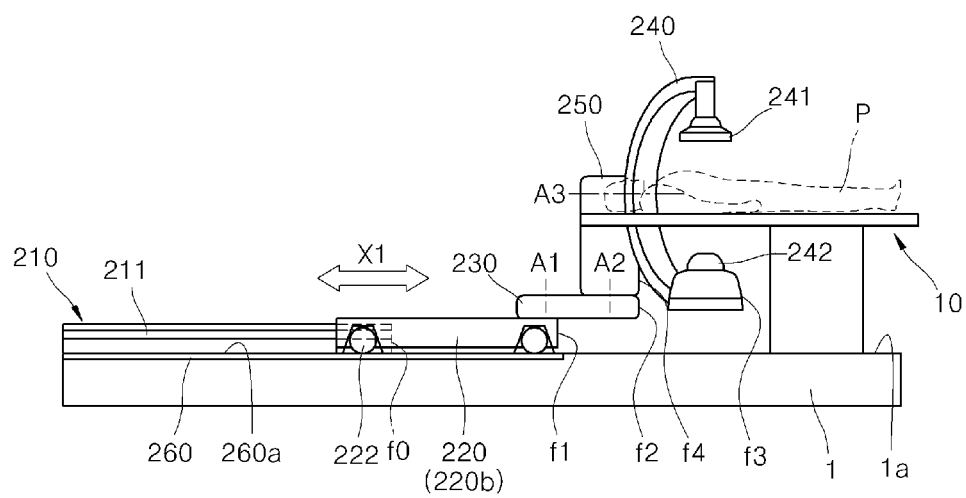
FIGS. 4 and 5 are a side view and a plan view illustrating a state in which an imaging system of FIG. 1 moves in a first direction, respectively.
Figure 5:
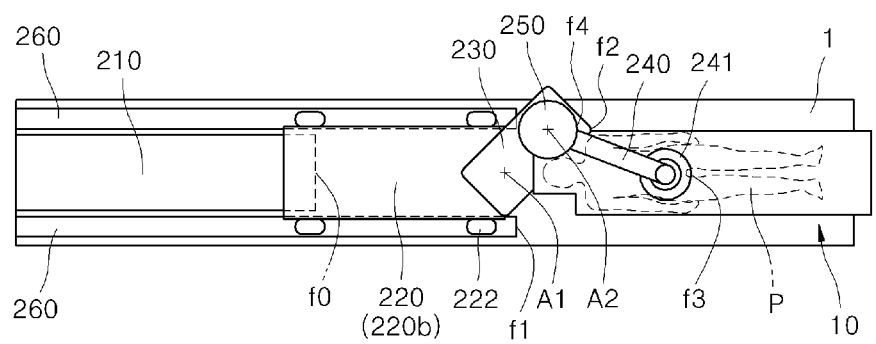

FIGS. 4 and 5 are a side view and a plan view illustrating a state in which the imaging system 20 of FIG. 1 moves in the first direction X1, respectively. A position relationship between the transfer frame 220 and the other elements when the transfer frame 220 moves between the first and second positions 220a and 220b will now be described with reference to FIGS. 1 to 5.

Referring to FIGS. 1 and 2, when the imaging system 20 is not used, the transfer frame 220 is disposed at the first position 220a. The first position 220a may be a position during which the imaging system 20 is in a parking state where the imaging system 20 is not used. When the transfer frame 200 is disposed at the first position 220a, respective front ends f1 to f4 of the transfer frame 220 and the first to third rotary arms 230, 240 and 250 may be disposed so as not to protrude in a direction from a front end f0 of the fixing frame 210 to the examination table 10. For example, the respective front ends f1 to f4 of the transfer frame 220 and the first to third rotary arms 230, 240 and 250 may be retracted or disposed farther away from the examination table 10 than the front end f0 of the fixing frame 210. Here, each of the front ends is defined as an end portion in a direction closest to the examination table 10.

Referring to FIGS. 4 and 5, when an image processing operation is performed by the imaging system 20, the transfer frame 220 is disposed at the second position 220b. In this case, the front end f1 of the transfer frame 220 protrudes or extends in a direction from the front end f0 of the fixing frame 210 to or toward the examination table 10. For example, the front end f1 of the transfer frame 220 is disposed closer to the examination table 10 than the front end f0 of the fixing frame 210. Also, the respective front ends f2 to f4 of the first to third rotary arms 230, 240 and 250 protrude in the direction from the front end f0 of the fixing frame 210 to the examination table 10. In this case, at least one of the radiation source 241 and radiation detector 242 of the second rotary arm 240 overlaps the examination table 10.

When the transfer frame 220 moves between the first and second positions 220a and 220b, for example, when the transfer frame 220 moves with the front end of the transfer frame 220 protruding from the fixing frame 210, the rolling member 222 supports a weight of the transfer frame 220, and guides movement of the transfer frame 220 in the first direction X1. Since the rolling member 222 supports the weight (for example, weight of about 200 Kg to about 300 Kg) of the transfer frame 220, the transfer frame 220 moves in the first direction X1 without being shaken in a vertical direction.

The rolling member 222 may move in the first direction X1 in contact with a supporting member 260. The supporting member 260 may extend along the first direction X1 to support movement of the rolling member 222.

In the supporting member 260, a top surface facing the rolling member 222 is a planar surface. Therefore, the supporting member 260 may vertically support the rolling member 222 without being shaken. This is because when the rolling member 222 directly contacts the floor 1 without contacting the supporting member 260, the transfer frame 220 is vertically shaken due to a bending of a floor surface 1a.

The supporting member 260 may be formed of a material capable of supporting a load caused by the rolling member 222. For example, the supporting member 260 may include steel having certain strength. Therefore, despite repeated movement of the rolling member 222 in the first direction X1, the floor 1 is prevented from being damaged.

The supporting member 260 may be disposed on the floor 1 not to protrude from the floor surface 1a and in order for a top surface 260a of the supporting member 260 to match or be level with the floor 1. For example, the supporting member 260 may be buried in the floor 1 in order for the top surface 260a of the supporting member 260 to be disposed in parallel with the floor surface 1a. The supporting member 260 does not protrude from the floor surface 1a, thereby preventing the supporting member 260 from obstructing movement of a worker, a patient, and another medical apparatus.

Referring again to FIG. 1, the transfer frame 220 may include a sweeping member 270 that removes foreign materials from the top surface 260a of the supporting member 260. The sweeping member 270 moves according to movement of the transfer frame 220 with an end of the sweeping member 270 contacting the supporting member 260, thereby effectively removing foreign materials from the top surface 260a of the supporting member 260. The sweeping member 270 may be formed of a flexible material that is bent by a contact with the supporting member 260. Also, the sweeping member 270 may be disposed at a front end and/or a rear end in the first direction X1.

Figure 6:
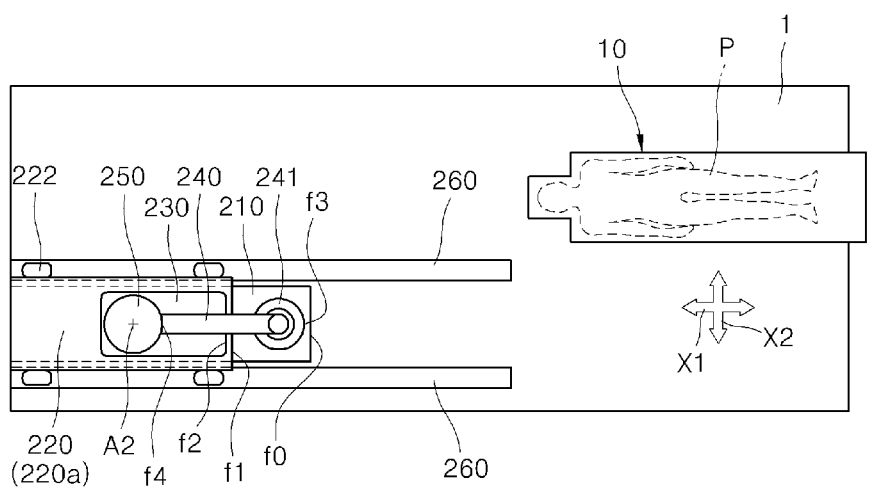
FIG. 6 is a plan view illustrating an example in which an arrangement of the fixing frame is modified in the radiation diagnostic apparatus of FIG. 2.

In the above-described embodiment, an example in which the fixing frame 210 is disposed in parallel with the examination table 10 along the length direction X1 as in FIG. 2 has been described above. However, the arrangement of the fixing frame 210 is not limited thereto, and as in FIG. 6, the fixing frame 210 may be disposed to be separated from (and somewhat beside) the examination table 10 in a second direction X2 intersecting the first direction X1.

Figure 7:
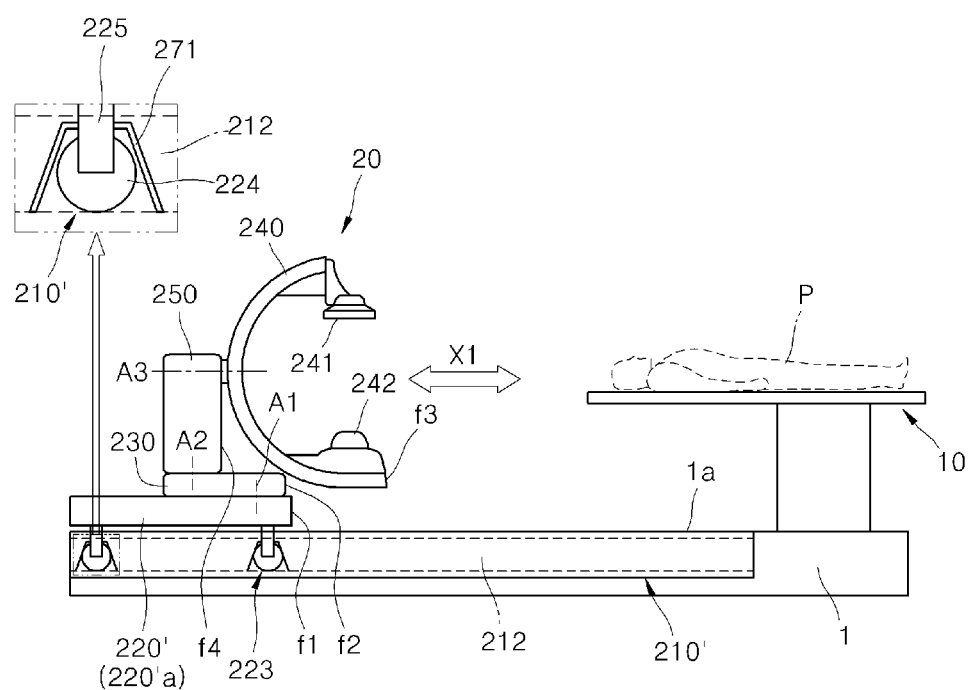
FIG. 7 is a view schematically illustrating a radiation diagnostic apparatus according to another embodiment.
Figure 8:
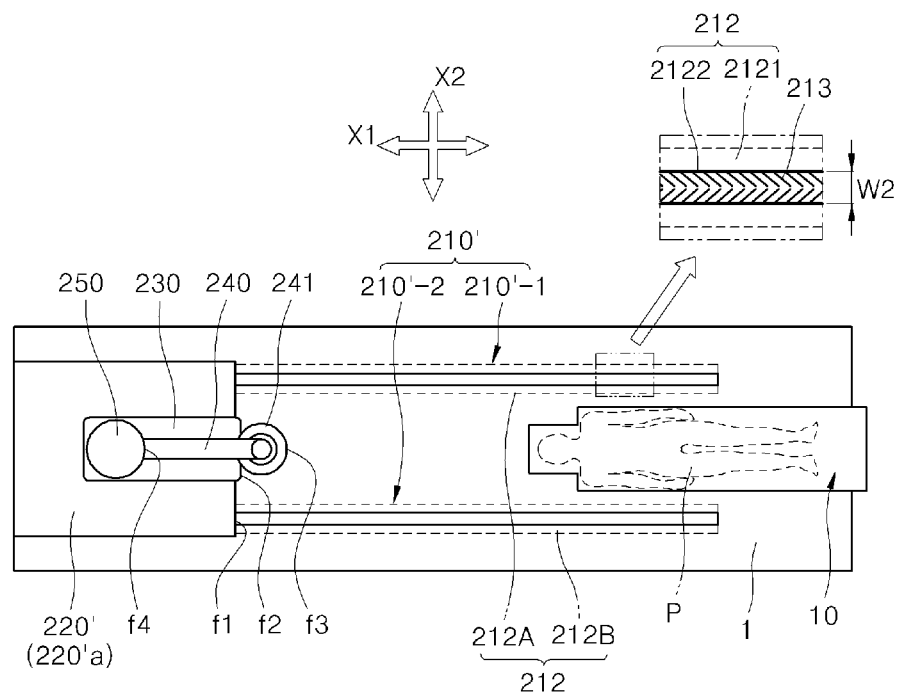
FIG. 8 is a plan view illustrating the radiation diagnostic apparatus of FIG. 7.
Figure 9:
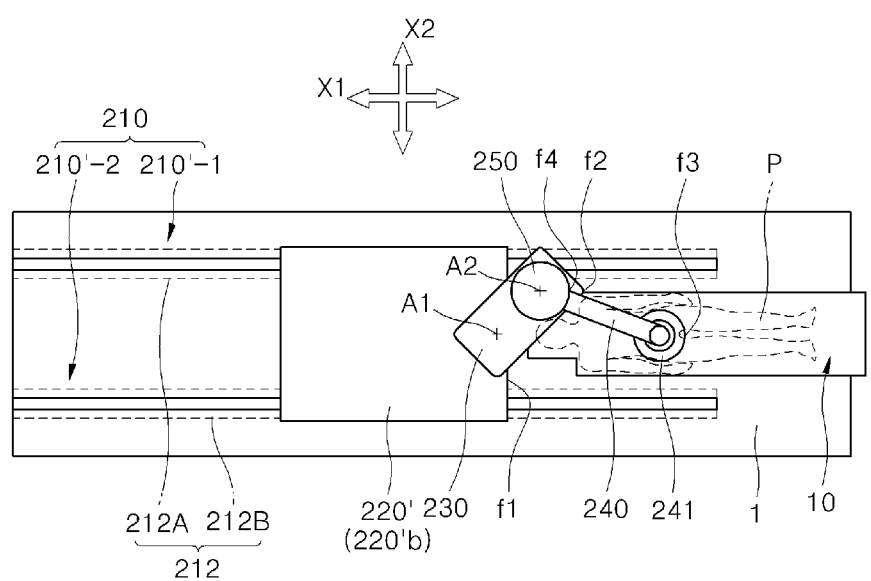
FIG. 9 is a view illustrating a state in which an imaging system of FIG. 8 moves in a first direction.
Figure 10:
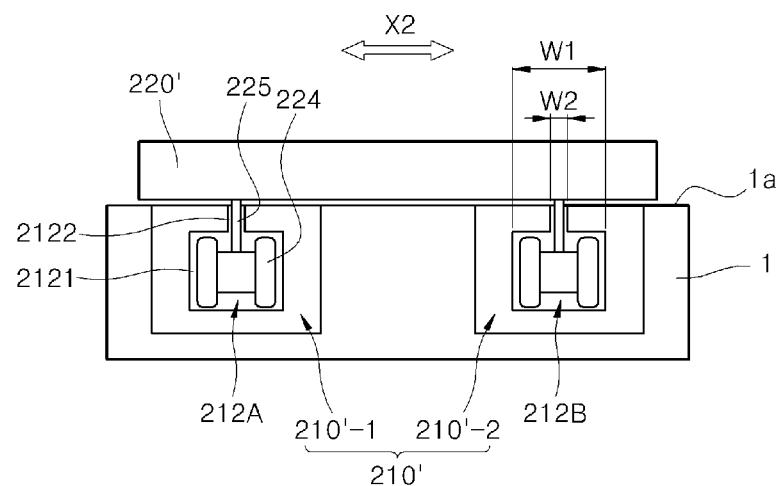
FIG. 10 is a cross-sectional view schematically illustrating a transfer frame and a fixing frame which are illustrated in FIG. 7.

FIG. 7 is a view schematically illustrating a radiation diagnostic apparatus according to another embodiment. FIG. 8 is a plan view illustrating the radiation diagnostic apparatus of FIG. 7. FIG. 9 is a view illustrating a state in which an imaging system 20 of FIG. 8 moves in a first direction X1. FIG. 10 is a cross-sectional view schematically illustrating a transfer frame 220' and a fixing frame 210' which are illustrated in FIG. 7.

Referring to FIGS. 7 to 9, the radiation diagnostic apparatus includes an examination table 10 and an imaging system 20 that generates an image of an object P located on the examination table 10. The imaging system 20 includes a fixing frame 210', a transfer frame 220', a first rotary arm 230, a second rotary arm 240, and a third rotary arm 250. In the above-described prior embodiment and the present embodiment, like reference numerals refer to like elements, and repetitive descriptions are not provided. The following description will focus on differences between the above-described prior embodiment and the present embodiment described in more detail below.

The transfer frame 220' may move in a front direction (which becomes closer to the examination table 10) or a rear direction (which deviates or separates from the examination table 10) along the first direction X1 with respect to the fixing frame 210'.

The transfer frame 220' may move to a first position 220'a (see FIG. 8), at which respective front ends f1 to f4 of the transfer frame 220' and the first to third rotary arms 230, 240 and 250 are separated from the examination table 10, and a second position 220'b at which a portion (for example, at least one of a radiation source 241 and a radiation detector 241) of the second rotary arm 240 overlaps the examination table 10.

The present embodiments relate to a floor type radiation diagnostic apparatus in which the imaging system 20 that moves in the first direction X1 is disposed on a floor 1. Since the radiation diagnostic apparatus has a structure in which the imaging system 20 is disposed on the floor 1, it is required to consider a moving route of a patient or a worker (for example, a doctor or a nurse). Also, it is required to consider a moving path through which other medical apparatus moves.

The fixing frame 210' is buried in and fixed to the floor 1 so as not to protrude from a floor surface 1a. The fixing frame 210' guides movement of the transfer frame 220' in the first direction X1. To this end, the fixing frame 210' includes a guide groove 212 that is formed along the first direction X1. A moving member 223 may be inserted into the guide groove 212, and may move in the first direction X1 along the guide groove 212. The moving member 223 includes a rolling member 224 (for example, a wheel), which is rotatable, and a supporting shaft 225 that is fixed to the transfer frame 220' to support the rolling member 224. The guide groove 212 may include a first guide groove 212A and a second guide groove 212B that is separated from the first guide groove 212A in a second direction X2 intersecting the first direction X1.

Referring to FIG. 10, the fixing frame 210' may include a first fixing frame 201'-1, in which the first guide groove 212A is formed, and a second fixing frame 201'-2 in which the second guide groove 212B is formed. The first fixing frame 201'-1 and the second fixing frame 201'-2 may be disposed to be separated from each other in the second direction X2 intersecting the first direction X1.

Each of the first and second guide grooves 212A and 212B includes a first region 2121, in which the rolling member 224 moves, and a second region 2122 in which the supporting shaft 225 moves. In the first and second guide grooves 212A and 212B, a width w2 of the second region 2122 may be narrower than a width w1 of the first region 2121. To this end, an area exposed to the outside is minimized, thereby reducing foreign materials which may fall into the first and second guide grooves 212A and 212B. In the first and second guide grooves 212A and 212B, the width w2 of the second region 2122 may be set to a width through which the supporting shaft 225 passes and which does not obstruct or hinder movement of a patient, a worker, or the other medical apparatus. For example, in the first and second guide grooves 212A and 212B, the width w2 of the second region 2122 may be about 5 mm to about 30 mm, and for example, about 10 mm to about 20 mm. Here, the width w2 is defined as a width in a direction X2 intersecting the first direction X1.

When the moving member 223 moves along the first and second guide grooves 212A and 212B, the transfer frame 220' moves along the first direction X1 with respect to the fixing frame 210'. The rolling member 224 of the moving member 223 supports a weight of the transfer frame 220', and rotates according to movement of the transfer frame 220'.

Referring again to FIG. 8, in order to prevent foreign materials from penetrating into the first and second guide grooves 212A and 212B, a blocking member 213 may be provided in the each of first and second guide grooves 212A and 212B, and for example, in the second region 2122. The blocking member 213 may be formed of a flexible material that is bent by a contact with the supporting shaft 225 when the supporting shaft 225 of the moving member 223 moves.

Referring again to FIG. 7, the transfer frame 220' may include a sweeping member 271 that removes foreign materials from the inside of the guide groove 212, and for example, from the second region 2122. The sweeping member 271 moves according to movement of the transfer frame 220' with an end of the sweeping member 271 contacting a wall surface of the guide groove 212, thereby effectively removing foreign materials penetrating into or residing in the guide groove 212. The sweeping member 271 may be formed of a flexible material that is bent by a contact with the guide groove 212. Also, the sweeping member 271 may be disposed at a front end or a rear end of the moving member in the first direction X1.

Figure 11:
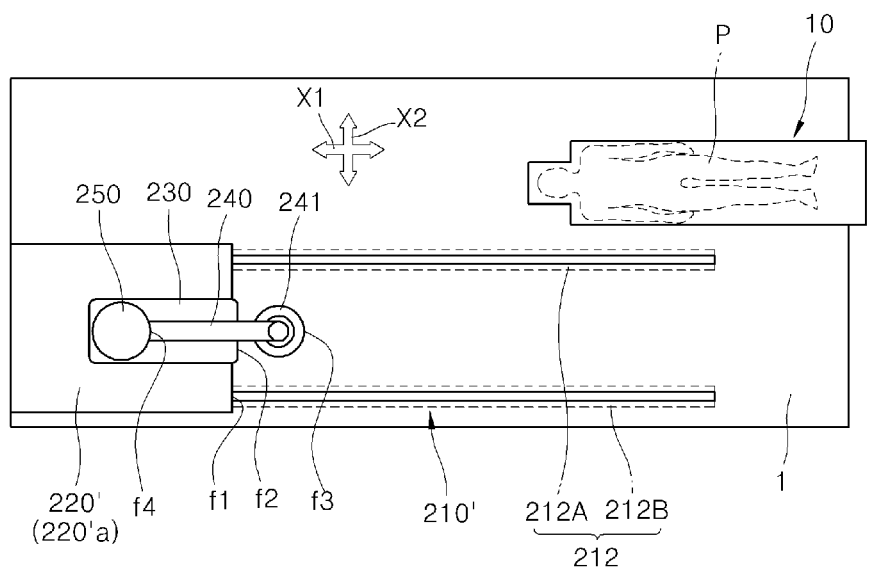
FIG. 11 is a plan view illustrating an example in which an arrangement of the fixing frame is modified in the radiation diagnostic apparatus of FIG. 8.

In the above-described embodiment, an example in which the fixing frame 210' is disposed in parallel with the examination table 10 along the length direction X1 as in FIG. 8 has been described above. However, the arrangement of the fixing frame 210' is not limited thereto, and as in FIG. 11, the fixing frame 210' may be disposed to be separated from the examination table 10 in the second direction X2 intersecting the first direction X1.

Figure 12:
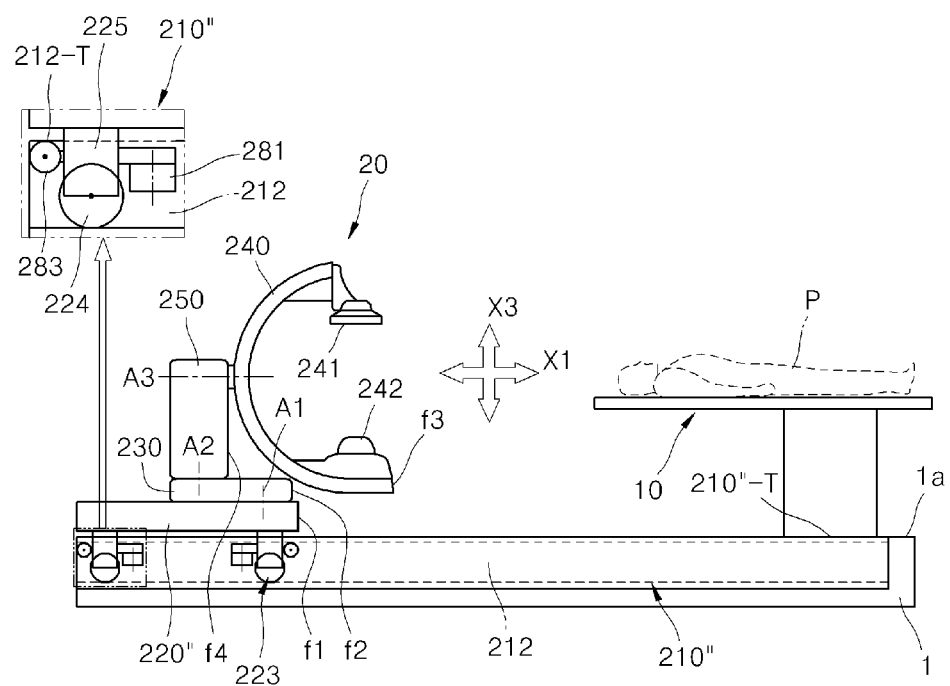
FIG. 12 illustrates a modification example of the embodiment of FIG. 7.
Figure 13:
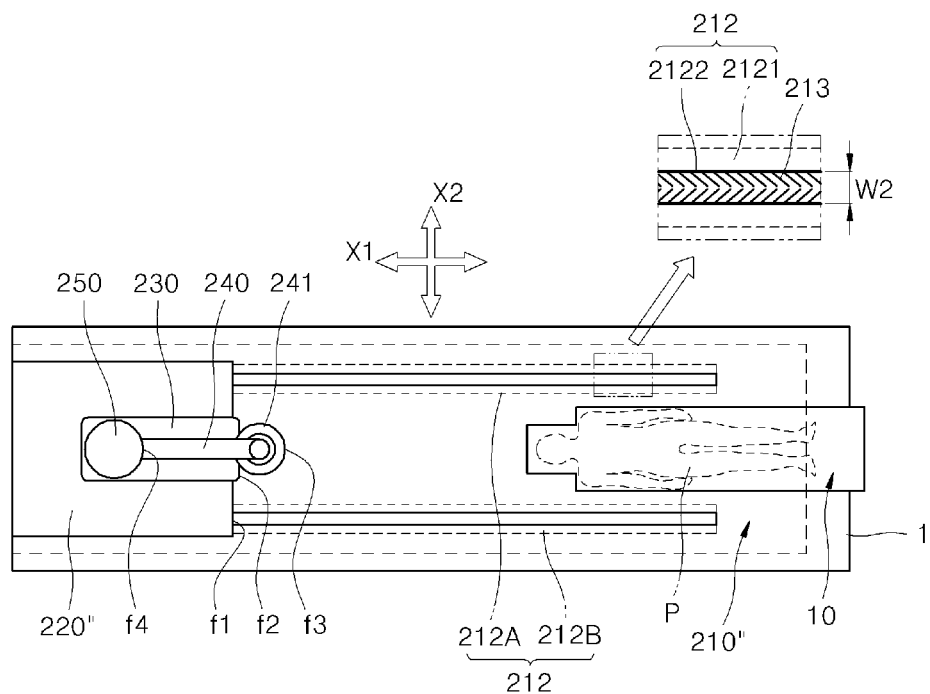
FIG. 13 is a plan view illustrating a radiation diagnostic apparatus of FIG. 12.
Figure 14:
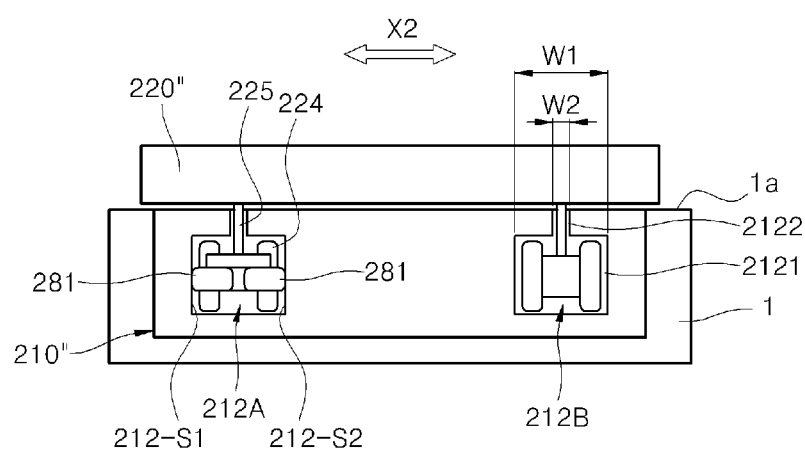
FIG. 14 is a view schematically illustrating a transfer frame and a fixing frame which are illustrated in FIG. 12.

FIG. 12 illustrates a modification example of the embodiment of FIG. 7. FIG. 13 is a plan view illustrating a radiation diagnostic apparatus of FIG. 12. FIG. 14 is a view schematically illustrating a transfer frame and a fixing frame which are illustrated in FIG.

The radiation diagnostic apparatus includes an examination table 10 and an imaging system 20 that generates an image of an object P located on the examination table 10. The imaging system 20 includes a fixing frame 210", a transfer frame 220", a first rotary arm 230, a second rotary arm 240, and a third rotary arm 250. The transfer frame 220" may move in a front direction (which becomes closer to the examination table 10) or a rear direction (which deviates or separates from the examination table 10) along a first direction X1 with respect to the fixing frame 210". In the above-described embodiment and the present embodiment, like reference numerals refer to like elements, and repetitive descriptions are not provided. The following description will focus on differences between the above-described embodiment and the present embodiment.

In the present embodiment, in consideration of accurate position movement of the imaging system 20, the following description will focus on a configuration for accurate position movement of the transfer frame 220" with respect to the examination table 10.

Referring to FIGS. 12 and 13, the fixing frame 210" may be a single member in which a first guide groove 212A and a second guide groove 212B are formed. Since the first guide groove 212A and the second guide groove 212B are formed in one member, separate work for setting a positional relationship between the first and second guide grooves 212A and 212B may not be performed when installing the first and second guide grooves 212A and 212B to the floor 1.

The fixing frame 210" may extend in a first direction X1 in order for at least one portion of the fixing frame 210" to overlap an examination table 10. The examination table 10 may be disposed on an upper portion 210"-T of the fixing frame 210". Since the examination table 10 is disposed on the upper portion 210"-T of the fixing frame 210", a height relationship between the examination table 10 and the transfer frame 220" moving along a guide groove 212 of the fixing frame 210" is accurately controlled. If the examination table 10 is disposed on a floor 1 instead of the fixing frame 210", separate work for adjusting a relative position between the examination table 10 and the transfer frame 220" may be performed. However, in the present embodiment, the separate work may not be performed.

The transfer frame 220" may include a plurality of shaking or wobbling prevention members 281 and 283 that prevent the transfer frame 220" from being shaken, wobbling or leaning in directions X2 and X3 intersecting the first direction X1. The shaking prevention members 281 and 283 may include a side shaking prevention wheel 281 and an upper shaking prevention wheel 283.

Referring to FIG. 14, the side shaking prevention wheel 281 may be provided in at least one of the first and second guide grooves 212A and 212B. For example, as illustrated, the side shaking prevention wheel 281 may be provided in the first guide groove 212A. However, an arrangement of the side shaking prevention wheel 281 is not limited to the first guide groove 212A, and for example, the side shaking prevention wheel 281 may be provided in only the second guide groove 212B or both the first and second guide grooves 212A and 212B. The side shaking prevention wheel 281 contacts both sides 212-S1 and 212-S2 of the first guide groove 212A, and rotates according to movement of the transfer frame 220" in the first direction X1. The side shaking prevention wheel 281 prevents the transfer frame 220" from being shaken in the second direction X2 intersecting the first direction X1.

Referring again to FIG. 12, the upper shaking prevention wheel 283 may be provided in at least one of a front end and a rear end of the transfer frame 220". The upper shaking prevention wheel 283 contacts a top 212-T of the guide groove 212, and rotates according to movement of the transfer frame 220" in the first direction X1. The upper shaking prevention wheel 283 rotates in a state of contacting the top 212-T of the guide groove 212, and thus, even when external force is applied to the transfer frame 220" in the third direction X3 intersecting the first direction X1, the transfer frame 220" is not shaken in the third direction X3. Although not shown, the upper shaking prevention wheel 283 may be directly supported by a floor of the transfer frame 220", or may be supported through a supporting shaft 225.

In the above-described embodiment, an example in which the first and second guide grooves 212A and 212B of the fixing frame 210" are illustrated in parallel with the examination table 10 in the first direction X1 has been described above. However, although not shown, the first and second guide grooves 212A and 212B may not be disposed in parallel with the examination table 10 in the first direction X1, and for example, the first and second guide grooves 212A and 212B may be disposed to be separated from the examination table 10 in the second direction X2. In this case, a width of the fixing frame 210" in the second direction X2 may increase in order for the examination 10 to be disposed on a top of the fixing frame 210". Also, in the present embodiment, although not shown, the fixing frame 210" may include a sweeping member that removes foreign materials from the inside of the guide groove 212.

As described above, according to the one or more of the above embodiments, the radiation diagnostic apparatus performs an accurate diagnosis without moving a patient in a diagnostic process, and minimizes a moving restriction of a worker in a non-diagnostic process.

To aid in understanding the embodiments, reference numerals are used in the exemplary embodiments shown in the drawings, and specific terms are used to explain the exemplary embodiments; however, they are not intended to limit the embodiments and may represent all the components that could be considered by those skilled in the art.

Specific executions described herein are merely examples and do not limit the scope of the embodiments in any way. For simplicity of description, other functional aspects of conventional electronic configurations, control systems, software and the systems may be omitted. Furthermore, line connections or connection members between elements depicted in the drawings represent functional connections and/or physical or circuit connections by way of example, and in actual applications, they may be replaced or embodied as various additional functional connection, physical connection or circuit connections. Also, the described elements may not be inevitably required elements for the application of the embodiments unless they are specifically mentioned as being "essential" or "critical." The term "include" or "comprise" used herein should not be interpreted to include all the various stages of the various components described in the specification, or the components some of them or some of these steps It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope thereof as defined by the following claims.

What is claimed is:

1. A radiation diagnostic apparatus, comprising:
an examination table that has a length in a first direction and is disposed to be fixed to a floor;
a fixing frame that protrudes from a surface of the floor and is fixedly disposed on the floor to be separated from the examination table in the first direction, and comprises a guide member extending along the first direction;
a transfer frame that contacts the guide member, and that moves along the first direction with respect to the fixing frame;
a first rotary arm that is rotatably connected to the transfer frame; and
a second rotary arm that is rotatably connected to the first rotary arm, and that is provided for a radiation source and a radiation detector to face each other,
wherein the transfer frame moves to a first position, at which a front end of the transfer frame overlaps the fixing frame, and a second position at which the front end of the transfer frame does not overlap the fixing frame, and wherein the transfer frame is disposed at the first position, a transfer frame front end, a first rotary arm front end and a second rotary arm front end are disposed farther away from the examination table than a fixing frame front end of the fixing frame.

2. The radiation diagnostic apparatus of claim 1, wherein when the transfer frame is disposed at the second position, a transfer frame front end is disposed closer to the examination table than the fixing frame front end of the fixing frame.

3. The radiation diagnostic apparatus of claim 1, further comprising at least one rolling member that supports a weight of the transfer frame, and rotates according to movement of the transfer frame.

4. The radiation diagnostic apparatus of claim 2, further comprising a supporting member that supports the rolling member, is formed to be extended in the first direction, and is disposed in the floor for a top of the supporting member to match a surface of the floor.

5. The radiation diagnostic apparatus of claim 4, further comprising a sweeping member that removes foreign materials from the supporting member.

6. A radiation diagnostic apparatus, comprising:
an examination table that has a length in a first direction and is disposed to be fixed to a floor;
a fixing frame that is buried in and fixed to the floor to not protrude from a surface of the floor, and that includes at least one guide groove extending along the first direction to define a space in the floor;
a transfer frame that includes a moving member inserted into the guide groove, and that moves along the first direction with respect to the fixing frame;
a first rotary arm that is rotatably connected to the transfer frame; and
a second rotary arm that is rotatably connected to the first rotary arm, and that is provided for a radiation source and a radiation detector to face each other,
wherein the moving member comprises a rolling member that is rotatable and a supporting shaft that supports the rolling member,
the at least one guide groove comprises a first region in which the rolling member moves and a second region in which the supporting shaft moves, and
in the at least one guide groove, a width of the second region is narrower than a width of the first region.

7. The radiation diagnostic apparatus of claim 6, further comprising a blocking member that is provided in the second region, and that prevents foreign materials from penetrating from an outside.

8. The radiation diagnostic apparatus of claim 6, wherein the transfer frame further comprises a sweeping member that removes internal foreign materials of the at least one guide groove.

9. The radiation diagnostic apparatus of claim 6, wherein the fixing frame is disposed to be separated from the examination table in a second direction intersecting the first direction.

10. The radiation diagnostic apparatus of claim 6, wherein the at least one guide groove comprises a first guide groove and a second guide groove that is separated from the first guide groove in a second direction intersecting the first direction.

11. The radiation diagnostic apparatus of claim 10, wherein the fixing frame comprises:
a first fixing frame in which the first guide groove is formed; and a second fixing frame in which the second guide groove is formed.

12. The radiation diagnostic apparatus of claim 10, wherein the fixing frame is a single member in which the first guide groove and the second guide grooves are formed.

13. The radiation diagnostic apparatus of claim 12, wherein,
the fixing frame extends in the first direction for at least one portion of the fixing frame to overlap the examination table, and
the examination table is disposed on a top of the fixing frame.

14. The radiation diagnostic apparatus of claim 6, wherein the transfer frame comprises a shaking prevention member that prevents the transfer frame from being shaken in a direction intersecting the first direction.

15. The radiation diagnostic apparatus of claim 14, wherein the shaking prevention member comprises a side shaking prevention member that contacts both sides of the guide groove, and that rotates according to movement of the transfer frame.

16. The radiation diagnostic apparatus of claim 14, wherein the shaking prevention member comprises an upper shaking prevention member that contacts a top of the guide groove, and that rotates according to movement of the transfer frame.

* * * * *